United States Patent [19]

Kaye

[11] 4,410,492

[45] Oct. 18, 1983

[54] STERILIZING METHOD INCORPORATING RECIRCULATION OF CHAMBER ATMOSPHERE

[75] Inventor: Saul Kaye, Evanston, Ill.

[73] Assignee: Ben Venue Laboratories, Inc., Bedford, Ohio

[21] Appl. No.: 378,505

[22] Filed: May 17, 1982

Related U.S. Application Data

[63] Continuation-in-part of Ser. No. 212,972, Feb. 13, 1981, Pat. No. 4,337,223.

[51] Int. Cl.³ .............................................. A61L 2/20
[52] U.S. Cl. ...................................... 422/27; 422/34; 422/112
[58] Field of Search ................... 422/27, 28, 33, 34, 422/38

[56] References Cited

U.S. PATENT DOCUMENTS

| | | | |
|---|---|---|---|
| 3,035,886 | 5/1962 | Hickey | 422/27 |
| 3,163,494 | 12/1964 | Kaye | 422/34 X |
| 3,490,863 | 1/1970 | Schumann et al. | 422/34 X |
| 3,561,918 | 2/1971 | Ray | 422/34 X |
| 3,598,516 | 8/1971 | Shull et al. | 422/27 |
| 3,963,438 | 6/1976 | Banez | 422/31 |

FOREIGN PATENT DOCUMENTS 2435037 1/1976 Fed. Rep. of Germany ........ 422/27

OTHER PUBLICATIONS

Pickerill, J. K., "Practical System for Steam-Formaldehyde Sterilizing"; *Lab. Pract.* (GB); vol. 24; No. 6; 6/75; pp. 401–404.

*Primary Examiner*—Barry S. Richman
*Attorney, Agent, or Firm*—Robert Bruce Henn

[57] ABSTRACT

A method for sterilizing medical devices is disclosed. The method comprises the circulation of a sterilant gas through a contaminated device bacteriologically to sterilize exposed surfaces, permitting the sterilant gas to remain within the lumen of the device for an effective period of time, and thereafter removing the sterilant gas by purging with sterile air or other inert gas.

5 Claims, 3 Drawing Figures

STERILIZING METHOD INCORPORATING RECIRCULATION OF CHAMBER ATMOSPHERE

CROSS-REFERENCE TO RELATED APPLICATION

This application is a continuation-in-part of my copending application Ser. No. 212,972, filed Feb. 13, 1981, now U.S. Pat. No. 4,337,223, issued June 29, 1982.

BACKGROUND OF THE INVENTION

1. Field of the Invention

The present invention is in the field of methods for effecting sterilization of medical devices; more particularly, this invention is in the field of methods for sterilizing medical devices by the circulation of a sterilant gas over and through the device, wherein the sterilant gas remains within the lumen of the apparatus for an effective period of time.

2. Description of the Prior Art

The need to sterilize instruments and apparatus for use in medicine, agriculture and fermentation industries was known even before the germ theory of disease was established. Heat, steam and a variety of chemicals were observed to be able to inactivate spoilage and disease-producing entities; many machines and methods of applying these sterilizing agents entered the literature in the early years of microbiology. In recent years, steam and ethylene oxide vapor have become the most widespread sterilizing agents, with the latter being used primarily to treat materials which are susceptible to damage by heat or moisture. It is important in such processes to supply the necessary concentrations of steam or vapor for sufficient times at elevated temperatures to inactivate all the microorganisms both on and within the material being tested.

The use of ethylene oxide to sterilize heat-sensitive medical equipment was first described thirty years ago, in Kaye, S.: The Use of Ethylene Oxide for the Sterilization of Hospital Equipment; J. Lab. Clin. Med. vol. 35, 823–828 (1950). Since that time, this has become the only practical alternative to heat treatment, and the requirements for successful sterilization have been thoroughly documented. There are required, at the contaminated surface, the following:

(1) A sufficient concentration of ethylene oxide vapor
(2) A relative humidity of between 20% and 70%
(3) As high a temperature as the goods will stand
(4) Enough exposure time to effect sterilization, and
(5) Time to desorb the gas from the materials which absorb it, in order to eliminate toxic effects when the instrument is used.

The importance of each and all of these parameters has been discussed in hundreds of publications and dozens of patents, whose contents are known to those skilled in the art of sterilization. Where the objects to be sterilized possess simple configurations, so that gas, heat and moisture may readily reach all contaminated areas, they may simply be placed in a chamber where these conditions are met, and no problems arise. However, even with objects whose contaminated surfaces are readily accessible to the sterilizing atmosphere, a great many precautions must be taken to assure sterilization. These precautions include, e.g., the removal of air from the sterilizer chamber to as great a degree as possible or practical, provision of packaging materials permeable to the sterilizing agent, arrangement of packaged goods to facilitate contact by the sterilizing agent with the object, etc.

Efforts have been made in designing objects which require sterilization to make it easy for sterilizing vapors to contact, diffuse, permeate, or penetrate into all the internal as well as the external contaminated sites. However, due to their purpose and nature, some medical devices necessarily contain very long and very narrow tubules, or lumens, requiring heating and penetration by sterilizing vapors, which vapors must also contact all of the exterior surfaces of the device. Examples of such devices are catheters and endoscopic instruments. Endoscopes are included in the class of instruments which ordinarily cannot be sterilized in an autoclave. Because they must be inserted into a natural orifice or an incision, endoscopes are necessarily small, ranging up to no more than about 16 millimeters (mm) in diameter at the end used for insertion, treatment or manipulation. Within the main tube are disposed other tubes for viewing, illumination, irrigation and suction; each of these tubes is therefore smaller than the outer tube, and may be of the order of 1 mm.

In instruments such as endoscopes, therefore, there is considerable delay in achieving all the desired conditions for effective ethylene oxide sterilization; thus, water, heat, and ethylene oxide vapor take a considerable time to reach the contaminated locations within the narrow lumens of long tubes, and there is a concomitantly longer time required for the toxic sterilizing gas to diffuse out of such passages. This invention is directed to a method for speeding up contact of heat, gas, and water vapor to such inaccessible locations, and for removing the gas rapidly after sterilization has been accomplished.

SUMMARY OF THE INVENTION

The present invention comprises a method for effecting sterilization of medical devices, by exposing the interior and exterior surfaces of the device to a sterilant fluid, maintaining the device at a temperature sufficient to effect sterilization in the presence of the sterilant fluid, maintaining the sterilant, within the lumen of the instrument for an effective length of time, and thereafter desorbing the sterilant fluid from the exposed surfaces, preferably by passing sterile air thereover.

DESCRIPTION OF THE PREFERRED EMBODIMENTS

Figure 1:
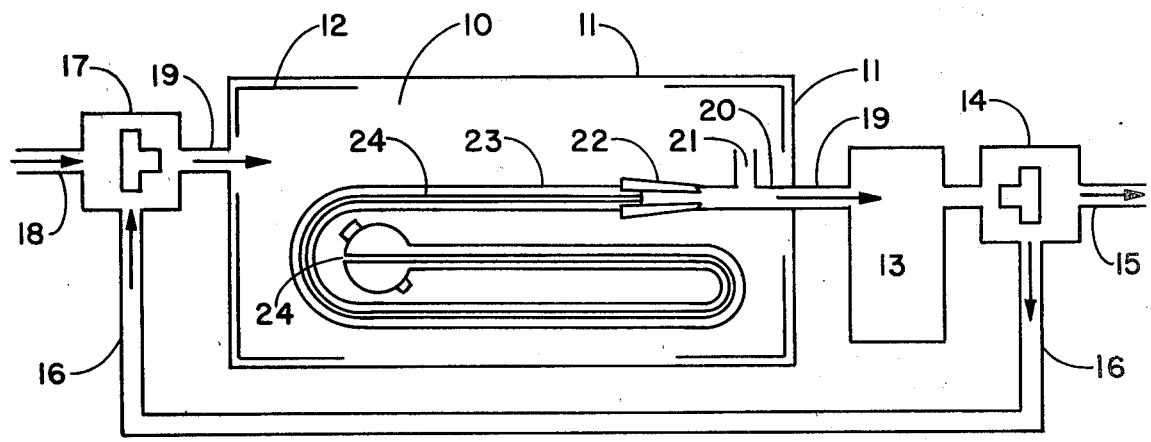
FIG. 1 is a view in section of apparatus useful in the practice of the present invention.

A portion of the atmosphere of a sterilizing chamber is continuously removed from the chamber by means of a pump, and returned to it by an external circuit. A minor portion of this recirculated flow is drawn through the narrow tubules of a device to be sterilized, causing these surfaces to be exposed to the same chamber conditions as are the exterior surfaces of the device. Objects are exposed to sterilizing atmospheres in such a way that even though they contain long and narrow hollow tubes, the surfaces of such tubes will be sterilized at the same time as the exterior surfaces of the object. This invention provides a means of simultaneously exposing both inner and outer surfaces of simple or long and complex structures to the temperatures and vapor conditions which exist in a sterilizing chamber.

The present invention comprises introducing a contaminated object or device into a chamber, sealing the chamber, removing the atmosphere, heating the chamber, introducing a sterilant gas, causing the gas to circulate and recirculate through and around the object or device, leaving the gas within the lumen of the device for an effective and sufficient time to effect sterilization, removing the sterilant gas, and thereafter admitting sterile air or other gas.

Air must be removed as much as is practically possible from the environs of the contaminated surface, not only to minimize dilution of the sterilizing vapor, but to raise the temperature of that surface as rapidly as possible. The manner in which air interferes with this temperature rise is known to those skilled in the art, and is set forth here for a more complete understanding of the normal course of events which occur in an ethylene-oxide-gas sterilizing cycle.

1. The sterilizer jacket is warmed to a pre-set elevated temperature, usually measured at the wall, before the chamber is opened to receive the objects to be sterilized.

2. The chamber door is opened, and the objects are placed therein. The objects are usually wrapped in muslin, paper, plastic or composite packages specially designed to maintain internal sterility after removal from the chamber, and during transportation and storage. In hospital and other medical gas sterilizers, these packages and their contents are usually at room temperature. In industrial gas sterilizers, a long period of heating and humidifying usually precedes loading in the chamber, so that the temperature of the object is close to that desired during the sterilization.

3. The chamber door is closed and water vapor is admitted to provide the desired relative humidity in the chamber.

4. A vacuum of from about 20 to about 25 inches of mercury (in. Hg) is drawn in the chamber before, during, or after the humidification.

5. Ethylene oxide vapor is admitted to the chamber in quantities which produce chamber pressures either less than, equal to, or greater than atmospheric pressure.

6. The goods are held in the chamber, the chamber walls being heated to maintain chamber temperature, for the period of time appropriate to attain sterilization.

7. The chamber contents are vented to the atmosphere.

8. Air, sterilized by filtration, is passed through the chamber and out through the vent, moved either by pressure or vacuum, to flush residual gas out of the chamber.

9. The door is opened and the goods removed.

Steps 3, 4 and 5 usually occupy but a short time by comparison with step 6. In step 6, the goods are exposed to ethylene oxide gas and to elevated temperature. It is evident that gas and heat must reach each possibly contaminated surface, and the more rapidly this occurs, the shorter the exposure (step 6) needs to be. Packaging and arrangement of objects in the chamber are designed to maximize gas and heat contact, but in some instances, these precautions are of little help.

Thus, objects containing long and narrow tubes, which are made of plastic, a poor heat conductor, buried in plastic or rubber coatings, which are poor heat conductors, filled originally with air, an effective insulator, at room temperature, present particularly great barriers to temperature equilibration with the chamber atmosphere when exposed in the usual types of sterilizers.

FIG. 1 is a sectional view of apparatus useful in the method of the present invention; the chamber is shown generally at 10. The walls 11 are rigid and impervious to gas. A door or similar opening, not shown in FIG. 1, is provided in the apparatus, to permit the introduction and removal of the materials to be sterilized. Gasket 12 is provided to effect a gas-tight seal when the door is closed. Those skilled in the art will realize that the door can provide an opening for the entire area of the apparatus, or only a portion thereof, so long as the internal parts of the apparatus are conveniently accessible.

Pump 13 permits the pressure within the apparatus to be modified as necessary, either above, at or below ambient pressure. Valve 14, depending on its attitude, serves to pass the chamber contents either through vent 15 to the atmosphere, or to recirculating tube 16. Second valve 17 is disposed to recirculate the chamber atmosphere back into chamber 10 through line 19. Air-bleed line 18 permits the introduction of atmospheric air as desired through second valve 17.

Those skilled in the art will realize that first valve 14 and second valve 17 can be operated in appropriate relationship to permit chamber 10 to be evacuated, to recirculate the chamber atmosphere, or to admit air or other gas to the chamber. In the operation of the method of the present invention, the relative positions of the valves are preferably programmed in a pre-set sequence; the valves can be moved to a given position by external means such as a solenoid, fluid-operated piston or the like. Such means are well known to those skilled in the art, and need not be further described in detail here. In similar fashion, recirculation of the gas within the chamber can be done by a pump, fan or other means known in the art for moving a gas.

Figure 2:
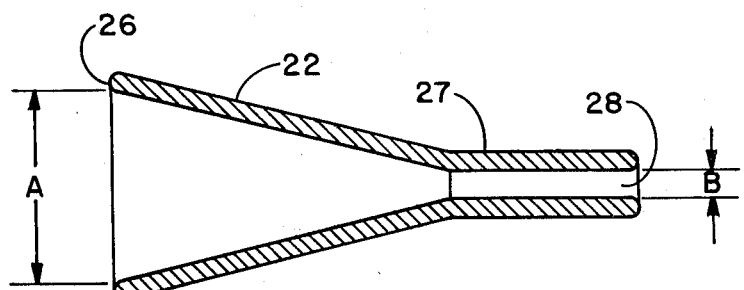
FIG. 2 is a sectional view of the holder used with the apparatus.

Socket or gripping device 22 is shown in a sectional view in FIG. 2. Wide end 26 has a diameter, dimension A, sufficient to accept a narrow end of e.g., an endoscope, and is about 20 mm., although a greater or lesser diameter may be used, depending on the particular device to be sterilized. Socket 22 is preferably made of an elastomeric material, and T-tube connection 28 is chosen to provide a substantially gas-tight seal on being placed over one part of T-tube 20, referring to FIG. 1. Dimension B at the narrow end 27 of socket 22 is about 3 mm or smaller in its internal diameter, and is generally, although not necessarily, of the same diameter as connection 28.

Figure 3:
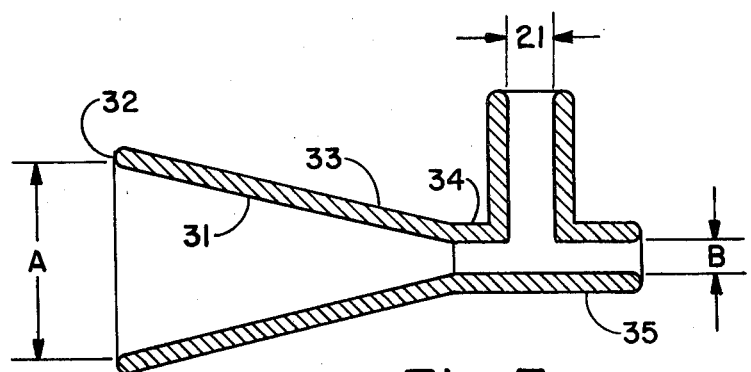
FIG. 3 is a sectional view of the holder and T-tube combined.

FIG. 3 is a sectional view of another embodiment of the socket or gripping device in combination with the T-tube. Holder 31 comprises a wide end 32 and a narrow end 33, the narrow end being integral with T-tube 34. As set forth hereinabove with respect to FIG. 2, holder 31 is preferably made of an elastomeric material, and is adapted to effect a gas-tight seal with line 19 shown in FIG. 1.

Temperature-control means to maintain the desired temperature for sterilization in connection with the method of the present invention are provided; such means are well known to those skilled in the art, and are not further described herein.

Means for the introduction of sterilant gas can include, e.g., a sealed container and unsealing means disposed either within chamber 10 or outside of it, suitable ducting and valving to introduce such gas into chamber 10 when appropriate, or other means known to those skilled in the art. One means for the introduction of sterilant gas into chamber 10 comprises disposing a sealed container of such gas within the chamber, and piercing the seal after the chamber air has been exhausted. At the temperatures used for sterilization, which range from about 20° to 70°, and preferably from about 30° to about 60° C., the preferred sterilant, ethylene oxide, is gaseous, and will boil from the container without the need for disposing the container at a particular attitude. Because some sterilant gases are more effective under conditions of enhanced humidity, means for introducing water, such as by first opening or piercing a container of water and then opening the container of sterilant gas, are provided. Alternatively, the water and sterilant can be introduced sequentially, either from separate containers, or by sequential introduction from exterior sources.

Pressure-control means are necessarily provided to maintain pressure at the level desired, and such means are within the knowledge of those skilled in the art.

In the operation of the method of the present invention, the aeration phase is performed by arranging valve 14 to pass the chamber atmosphere through vent 15 out to the atmosphere, and by arranging valve 17 to draw room air or other inert gas through tube 18 into the chamber by means of tube 19. In this arrangement, as was the case in the recirculation phase, the major portion of the gas enters pump 13 through the open arm of T-tube 20, and only a minor portion enters the pump after traversing the minute tubules 24 of the object 23 being sterilized. Air-bleed line 18 preferably has means for sterilizing the incoming air or other inert gas by passing it through a sterilizing field before it enters the chamber.

However, even though only a minor portion of the sterilizing vapor or air traverses the small tube 24, this small volume represents a considerable multiple of the internal volume of the tube. Thus, many gas exchanges occur within the tube during both sterilization and aeration phases, as described hereinbelow.

The effects of T-tube internal diameters and of various lengths of small tubing were measured experimentally. A diaphragm pump of the pressure-vacuum type was used to draw air through T-tubes of various sizes, and small tubules of several lengths. The rate of air passage through orifices substantially equivalent to orifice 21, and tubes substantially equivalent to tube 24, was measured for each combination, using an appropriate gas-flow meter. Four sizes of T-tubes were used; the three arms of each T-tube had identical lengths and internal diameters, as given in Table 1. The narrow-bore tubing was nominally 0.2 centimeter (cm) in size; the actual internal diameter was 0.193 cm. Three different lengths were tested: 91.5 cm, 183 cm and 366 cm.

The air temperature was 20° C.; airflow is reported in cubic centimeters (cc) per minute. The air exchanges effected inside the small tubes were calculated by dividing the measured volumes of air passed per minute by the internal volume of the tube sample being tested.

TABLE I

| T-tube I.D. (cm) | Length of Small Tube (cm) | Flow through orifice 21 (bypass) cc/min. | Flow through orifice 24 (small tube) cc/min. | Flow through small tube: air changes per minute |
| --- | --- | --- | --- | --- |
| 0.76 | 91.5 | 33,300 | 443 | 168 |
| 0.76 | 183.0 | 33,500 | 182 | 36 |
| 0.76 | 366.0 | 33,600 | 65 | 6 |
| 0.60 | 91.5 | 31,100 | 547 | 204 |
| 0.60 | 183.0 | 31,100 | 280 | 54 |
| 0.60 | 366.0 | 31,300 | 100 | 12 |
| 0.39 | 91.5 | 25,600 | 775 | 288 |
| 0.39 | 183.0 | 25,900 | 425 | 78 |
| 0.39 | 366.0 | 26,100 | 175 | 18 |
| 0.27 | 91.5 | 16,800 | 2,900 | 1,074 |
| 0.27 | 183.0 | 17,400 | 1,800 | 336 |
| 0.27 | 366.0 | 18,000 | 1,100 | 102 |

The results show that:
1. The smaller the internal diameter of the bypass tube, the more air traverses the small tubes; and
2. The longer the small tube, the greater resistance it offers to gas passage; therefore, less gas passes through.

During the sterilization phase, the relative amounts of sterilant gas going through the chamber, and going through the small tube, are of importance only as they affect the time needed to warm up the interior of the small tube. During the aeration phase when sterilant is being desorbed from all absorptive surfaces and fresh diluting air is being introduced into the chamber, the relative amounts of air going through and over devices containing long narrow tubes should be arranged in accordance with whether the interior or exterior surfaces are more absorptive of gas. Knowing the length and diameter of the internal tubes and the materials of construction of the device being treated, it is possible to select the proper size of bypass T-tube to decrease the necessary aeration time to a practical minimum. Thus, as the length of tube 24 increases, the internal diameter of T-tube 20 should be decreased to provide an acceptable amount of gas passage.

The socket or gripping device 22 can be provided in a number of modifications which will be evident to those familiar with the art, without departing from the scope and spirit of this invention.

It is desirable but not necessary that a single socket be able to hold objects of different outer diameters. Flexible endoscopes vary in their outer diameters from about 3 mm to more than 16 mm; with a socket of conical shape, this range of sizes is readily accommodated. In FIG. 2, conical socket 22 is shown in which the wide end 26, dimension A, is larger than 16 mm, and the narrow end 27, dimension B, is 3 mm or smaller. The socket is constructed of suitable material such as, e.g., poly(cis 1,4-isoprene) or other elastomer, and is connected at connection 28 to the T-tube 20 in FIG. 1.

Modification of socket 22 includes a T-tube bypass, shown generally at 31 in FIG. 3. Connecting end 35 is connected directly to line 19 in this embodiment. Device 23 is inserted into wide end 32, which is larger than 16 mm, and is gripped by some portion of socket 31 between wide end 32 and narrow end 33, whose diameter is less than 3 mm. Integral T-tube 34 permits gas by-pass as described above.

BACTERIOLOGICAL TEST OF THE METHOD AND APPARATUS

In certain endoscopic instruments there are contained one or more narrow tubes designed to carry water or air, to guide surgical or electrosurgical instruments and to remove biopsy samples from patients undergoing diagnostic or surgical procedures. Some of these tubes are as small as 1 mm in diameter, and as long as 3600 mm. These passageways, if left unsterilized, are capable of transmitting microorganisms to the interior of the patient's body. As indicated hereinabove, it is extremely difficult to raise the temperature inside such long narrow tubes, and to penetrate the entire length of the tubes with sterilizing quantities of chemical vapors.

For purposes of this experiment, simulated endoscopes, each 3600 mm in length, were prepared by threading lengths of poly(tetrafluoro)ethylene tubing 2 mm in diameter into lengths of poly(vinyl chloride) tubing with walls about 3.2 mm thick. The small annular space between the tubes at each end was sealed with a clay composition to assure that the sterilizing atmosphere contacted only the inner surfaces of the inner, poly(tetrafluoro)ethylene, tube, and did not enter that tube by diffusion through its walls from the annular space.

These endoscopes were contaminated by introducing five milliliters (ml) of water containing 100 million spores of Bacillus subtilis var. niger per ml, followed by five successive passages of 30 ml of sterile air, to distribute the spores on all internal surfaces. The endoscopes were then allowed to dry at 37° C. for two or more days before being subjected to the sterilizing method as described hereinabove in connection with the apparatus described in the drawings. The endoscopes, contained in a basket, were placed in chamber 10, the air in which had been heated to 57° C. One end of one of the endoscopes, representing instrument 23, was connected to socket 22; the T-tube 20 connected to the socket had an internal diameter of 7.6 mm in the arm connected to pump 13 through line 19, and the third arm, of the same diameter, was open to the interior of chamber 10. As shown by Table I, 65 cc of air pass through the endoscope 23, or two one-thousandths of the amount of air passing through the open arm of the T-tube 20. Prior to placement into chamber 10, both ends of both endoscopes were wrapped with sterile protective covering to prevent inadvertent contamination of the inner tube during handling and subsequent testing.

Three ml of water were added to the chamber, and the lid closed and latched. A vacuum of 24 in. Hg was drawn, and the sterilant gas, in this case, ethylene oxide, was introduced. The concentration of ethylene oxide within chamber 10 was sufficient to bring the interior pressure to about atmospheric.

After the ethylene oxide was vaporized, valves 14 and 17 were arranged to permit pump 13 to cause the chamber atmosphere to recirculate through recirculating tube 16. The major portion of the recirculated gas passed through the open end of T-tube 20, while a minor portion traversed the 3660-mm length of the narrow tube 24 in the endoscope 23 which was connected to the T-tube. As indicated, the second contaminated endoscope merely rested in chamber 10; no sterilant gas recirculated through this unit.

Both instruments were exposed to the action of the gas for 45 minutes at 57° C.; at the end of this time, the chamber atmosphere was purged of gas by pulling sterile air through chamber 10 and through the connected endoscopes removed for sampling.

Sampling was done by flushing the inner tube with 40 ml of sterile soybean-casein digest broth and flushing all retained broth from the lumen of the endoscope with sterile air. All the broth was caught in sterile glass tubes, and incubated for seven days at 37° C.

One day after incubation began, the broth used to flush the endoscope not subject to recirculation showed growth of B. subtilis. Therefore, these conditions were not sufficient to sterilize the interior of this endoscope. On the other hand, sterile broth irrigated through the "recirculated" tube emerged sterile and remained clear for seven days of incubation at 37° C.

Repetition of this experiment for increasing periods of time produced the results shown in Table II.

TABLE II

Exposure of Endoscopes to Ethylene Oxide Vapor at 57° C.
Contaminant = Spore of B. subtilis, $10^8$/ml;
five ml used per instrument.

| Description of Endoscope Exposure | Time of Exposure, Minutes | Results |
|---|---|---|
| In recirculation circuit | 45 | sterile |
| Not in recirculation circuit | 45 | non-sterile |
| Not in recirculation circuit | 90 | non-sterile |
| Not in recirculation circuit | 180 | non-sterile |
| Not in recirculation circuit | 360 | non-sterile |

Those skilled in the art will realize that providing recirculation of a sterilizing chamber atmosphere through a device containing narrow tubes produces conditions conducive to rapid sterilization, while the tubes in similar devices, exposed without recirculation, are not sterilized even in a much greater period of time.

Modifications, changes and improvements to the present forms of the invention herein disclosed, described and illustrated may occur to those skilled in the art who come to understand the principles and precepts thereof. Accordingly, the scope of the patent to be issued hereon should not be limited to the particular embodiments of the invention set forth herein, but rather should be limited only by the advance by which the invention has promoted the art.

I claim:

1. A method for sterilizing a medical instrument having passages therein comprising the steps of positioning said instrument totally within a sterilizing chamber, introducing a sterilant gas into said sterilizing chamber and exposing the interior and exterior surfaces of said instrument to said sterilant gas, said sterilant gas comprising an effective mixture of moisture and ethylene oxide, circulating and recirculating said sterilant gas through and around said instrument for a period of time to effect sterilization of said instrument, maintaining said instrument at a temperature between about 20° and about 70° C. during said step of circulating and recirculating said sterilant gas, and thereafter desorbing said sterilant gas from said surfaces of said instrument.

2. The method of claim 1 wherein said temperature is from about 30° to about 60° C.

3. The method of claim 1 wherein said step of desorbing comprises passing inert fluid over said exposed surfaces.

4. The method of claim 3 wherein said inert fluid comprises an inert gas.

5. The method of claim 3 wherein said inert fluid comprises air.

* * * * *